(12) United States Patent
Andersson

(10) Patent No.: US 6,660,879 B2
(45) Date of Patent: Dec. 9, 2003

(54) 3-ARYL-2-HYDROXYPROPIONIC ACID DERIVATIVE I

(75) Inventor: Kjell Andersson, Fjärås (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/039,868

(22) Filed: Jan. 4, 2002

(65) Prior Publication Data

US 2003/0027859 A1 Feb. 6, 2003

Related U.S. Application Data

(63) Continuation of application No. 09/861,163, filed on May 18, 2001, now abandoned, which is a continuation of application No. 09/341,904, filed on Jul. 20, 1999, now Pat. No. 6,258,850.

(30) Foreign Application Priority Data

Jun. 4, 1998 (SE) ................................................ 9801992

(51) Int. Cl.$^7$ .............................................. C07C 69/76
(52) U.S. Cl. ........................ 560/60; 562/470; 548/230
(58) Field of Search ..................... 514/571; 562/470; 560/60; 548/230

(56) References Cited

U.S. PATENT DOCUMENTS

| 5,232,945 A | | 8/1993 | Hulin | |
| 5,306,726 A | | 4/1994 | Hulin | |
| 6,048,883 A | * | 4/2000 | Haight et al. | 514/370 |
| 6,054,453 A | * | 4/2000 | Lohray et al. | 514/226.2 |

FOREIGN PATENT DOCUMENTS

| EP | 0428423 | 5/1991 |
| WO | 9119702 | 12/1991 |
| WO | 9731907 | 9/1997 |

OTHER PUBLICATIONS

STN International, File CAPLUS, CAPLUS accession No. 1997:684384; Sankyo Co., Ltd., et al: "Preparation of phenylalkyl–carboxylic acid derivatives lowering blood sugar level", WO,A1,9737970, 19971016.

Tetrahedron Letters, vol. 35, No. 19, 1994, Geoffrey G. Cox et al, "Competing O–H Insertion and Beta–Elimination in Rhodium Carbenoid Reactions; Synthesis of 2–Alkoxy–3–arylpropanoates", pp 3139–3142.

* cited by examiner

Primary Examiner—James H Reamer
(74) Attorney, Agent, or Firm—White & Case LLP

(57) ABSTRACT

A novel 3-aryl-2-hydroxypropionic acid derivative, a process and intermediate for its manufacture, pharmaceutical preparations containing it and the use of the compound in clinical conditions associated with insulin resistance.

6 Claims, No Drawings

3-ARYL-2-HYDROXYPROPIONIC ACID DERIVATIVE I

This application is a continuation of co-pending U.S. application Ser. No. 09/861,163, filed May 18, 2001 now abandoned, which is a continuation application of U.S. application Ser. No. 09/341,904, filed Jul. 20, 1999, now U.S. Pat. No. 6,258,850 B1.

FIELD OF INVENTION

The present invention releates to a novel 3-aryl-2-hydroxypropionic acid derivative, to a process and intermediate for preparing such a compound, having the utility in clinical conditions associated with insulin resistance, to methods for its therapeutic use and to pharmaceutical compositions containing it.

BACKGROUND OF THE INVENTION

Insulin resistance, defined as reduced sensitivity to the actions of insulin in the whole body or individual tissues such as skeletal muscle, myocardium, fat and liver prevail in many individuals with or without diabetes mellitus. The insulin resistance syndrome, IRS, refers to a cluster of manifestations including insulin resistance with accompanying hyperinsulinemia, possibly non insulin dependent diabetes mellitus (NIDDM); arterial hypertension; central (visceral) obesity; dyslipidemia observed as deranged lipoprotein levels typically characterized by elevated VLDL (very low density lipoproteins) and reduced HDL (high density lipoproteins) concentrations and reduced fibrinolysis.

Recent epidemiological research has documented that individuals with insulin resistance run a greatly increased risk of cardiovascular morbidity and mortality, notably suffering from myocardial infarction and stroke. In non-insulin dependent diabetes mellitus these atherosclerosis related conditions cause up to 80% of all deaths.

In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic derangements associated with IRS. To date, the treatment of NIDDM has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalize blood sugar but that will, if anything, further enhance insulin resistance and will not correct the other manifestations of IRS nor reduce cardiovascular morbidity and mortality. In addition such treatment involves a significant risk of hypoglycemia with associated complications.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitizing agents, such as the thiazolidinediones, which, at least in part, mediate their effects via an agonistic action on nuclear receptors. Ciglitazone is the prototype in this class. In animal models of IRS these compounds seem to correct insulin resistance and the associated hypertriglyceridaemia and hyperinsulinemia, as well as hyperglycemia in diabetes, by improving insulin sensitivity via an effect on lipid transport and handling, leading to enhanced insulin action in skeletal muscle, liver and adipose tissue.

Ciglitazone as well as later described thiazolidinediones in clinical development either have been discontinued reportedly due to unacceptable toxicity or show inadequate potency. Therefore there is a need for new and better compounds with insulin sensitizing properties.

PRIOR ART

Compounds of the formula

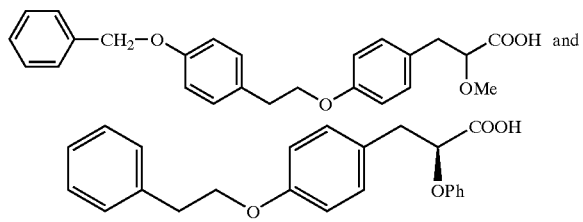

and certain derivatives thereof disclosed in U.S. Pat. No. 5,306,726 and WO 91/19702 are said to be useful as hypoglycemic and hypocholesterolemic agents, and in U.S. Pat. No. 5,232,945 said to be useful in the treatment of hypertension.

AU 650 429 discloses structurally related compounds, but claimed to have different properties: diuretic, antihypertensive, platelets anti-aggregating and anti-lipoxygenase properties.

EP 139 421 discloses compounds having the ability to lower blood lipid and blood sugar levels. Among these compounds is troglitazone, a compound that has reached the market for treatment of NIDDM or decreased glucose tolerance.

DESCRIPTION OF THE INVENTION

It has now surprisingly been found that the novel compound (S)-2-ethoxy-3-[4-(2-{4-methanesulfonyloxyphenyl}ethoxy)phenyl]propanoic acid having the formula I

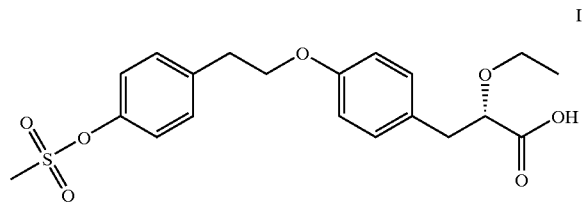

is effective in conditions associated with insulin resistance.

The invention also relates to pharmaceutically acceptable salts, solvates, such as hydrates, and crystalline forms of the compound of the formula I.

In the present specification the expression "pharmaceutically acceptable salts" is intended to define but is not limited to such salts as the alkali metal salts (e.g. sodium, lithium and potassium), alkaline earth metal salts (e.g. calcium, barium and magnesium), aluminium, zinc and bismuth salts, ammonium salts, salts with basic amino acids, such as arginine, lysine, and salts with organic amines such as ethanolamine, ethylenediamine, triethanoleamine, benzylphenethylamine, diethylamine, tromethamine, benzathine, chloroprocaine, choline, meglumine, procaine, clemizole and piperazine.

Throughout the specification and the appended claims, a given chemical formula or name shall encompass all pharmaceutically acceptable salts thereof, crystalline forms and solvates thereof such as for instance hydrates.

Methods of Preparation

The compound of the invention may be prepared as outlined below according to any of methods A–H. However, the invention is not limited to these methods, the compounds may also be prepared as described for structurally related compounds in the prior art.

A. The compound of the invention of the formula I, can be prepared by converting a compound of formula II

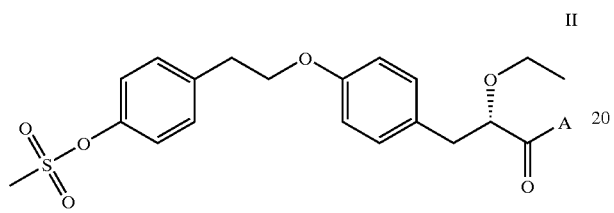

II wherein A is —OR$^p$, wherein R$^p$ is a protective group, e.g. ethyl, or A is a chiral auxiliary group, such as a chiral amine, e.g. (R)-fenylglycinol, a chiral alcohol, such as menthol or a chiral oxazolidinone, such as (S)-4-benzyl-2-oxazolidinone. The convertion can be performed as a hydrolysis which can be either acidic or basic and performed according to standard methods known to anyone skilled in the art or as described in the experimental part.

B. The compound of the formula I or the formula II, wherein A is a chiral auxiliary group or —OR$^p$ and R$^p$ is as defined above, can be prepared by reacting a compound of the formula III

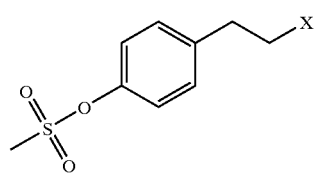

III wherein X is OH or a leaving group such as a sulfonate or a halogen, with a compound of the formula IV

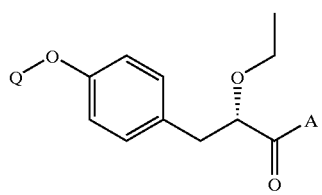

IV wherein Q is H and A is a chiral auxiliary group, —OH or —OR$^p$, and R$^p$ is as defined above. The reaction can be performed either by an alkylation reaction or a Mitsunobu reaction.

In an alkylation reaction the leaving group X can be a sulfonate such as mesylate, nosylate, tosylate, or a halogen, such as bromine or iodine. The compounds of formula III and IV, in approximately equimolar amounts or with an excess of either compound, are heated to reflux temperature in an inert solvent, such as isopropanol or acetonitrile, in the presence of a base, such as potassium carbonate or cesium carbonate.

The mixture is refluxed for the necessary time, typically between 0.5 h to 24 h, the work up procedure usually includes filtration, for removal of solid salt, evaporation, neutralisation (when A=OH) and extraction with water and an organic solvent such as dichloromethane, ethyl acetate, or diethyl ether.

The crude product is purified if desired e.g. by recrystallization or by standard chromatographic methods.

The Mitsunobu reaction can be carried out according to standard methods or as described in for example Tsunoda T., Yamamiaya Y., Ito S., Tetrahedron Letters, 34, 1639–1642 (1993) or O. Mitsunobu, Synthesis, 1981, p.1. When using a Mitsunobu reaction A can not be —OH.

In a typical Mitsunobu reaction a compound of formula III, wherein the group X is a hydroxyl group, and a compound of formula IV are mixed, in approximately equimolar amounts or with an excess of either compound, in an inert solvent, such as chloroform, dichloromethane, or tetrahydrofuran. A slight molar excess, 1–4 equivalents, of an azodicarboxylate, such as DEAD or ADDP and a phosphine (1–4 equivalents), such as tributylphosphine or triphenylphosphine are added and the reaction is stirred at a temperature high enough—for example room temperature—and a time long enough (1–24 hours) to obtain product, which can be worked up with standard literature methods and if desired purified, e.g. by standard chromatographic methods.

The compound of formula III can be prepared by standard procedures known to anyone skilled in the art, from commercially available starting materials or as described in the experimental section.

The compound of formula IV wherein Q is H and A is a chiral auxiliary group, —OH or —OR$^p$, wherein R$^p$ is as defined above, can be prepared as described below in the experimental part or by converting a compound of formula IV

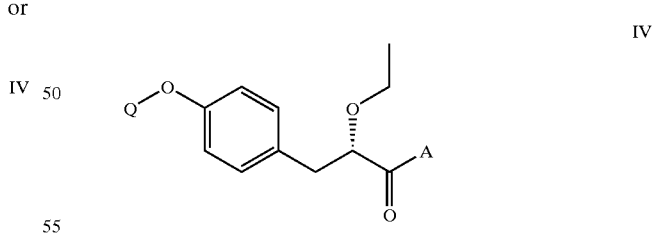

IV wherein Q is R$^q$, wherein R$^q$ is a protective group, e.g. benzyl, and A is a chiral auxiliary group, —OH or —OR$^p$ wherein R$^p$ is as defined above.

C. The compound of formula II wherein A is a chiral auxiliary group, and the compound of formula IV, wherein A is a chiral auxiliary group and Q is hydrogen or R$^q$, wherein R$^q$ is as defined above and, can be prepared by diastereoisomeric separation of the compound of the formula V

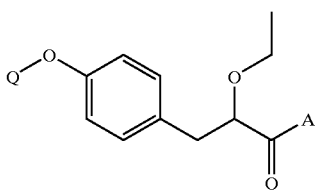

V wherein A is a chiral auxiliary group, Q is hydrogen, —CH$_2$CH$_2$Ph-4-OSO$_2$CH$_3$ or R$^q$, wherein R$^q$ is as defined above. The separation of the diastereomers can be performed either by crystallization or by chromatography. The chromatographic separation can be performed as described in the experimental part.

The compound of formula V wherein A is a chiral auxiliary group, Q is hydrogen, —CH$_2$CH$_2$Ph-4-OSO$_2$CH$_3$ or R$^q$, wherein R$^q$ is as defined above, can be prepared by converting a compound of formula VI

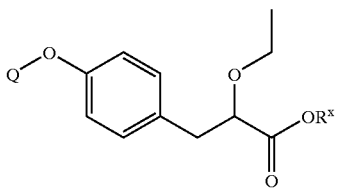

VI wherein Q is hydrogen, —CH$_2$CH$_2$Ph-4-OSO$_2$CH$_3$ or R$^q$, and R$^x$ is hydrogen or R$^p$, wherein R$^q$ and R$^p$ are as defined above, for example by reacting it with a chiral amine or a chiral alcohol.

The compound of formula V when A is a chiral amine can be prepared by reacting a compound of formula VI with a chiral amine such as (R)-phenyl glycinol for example in the presence of a peptide coupling system (e.g. EDC, DCC, HBTU, TBTU, PyBop or oxalylchloride in DMF), an appropriate base (e.g. pyridine, DMAP, TEA or DiPEA) and a suitable organic solvent (e.g. dichloromethane, acetonitrile or DMF) in accordance to methods well known to those skilled in the art or as described in the examples.

The compound of formula V when A is a chiral alcohol can be prepared in the same way using a chiral alcohol, such as menthol, instead of a chiral amine, or by the mixanhydride method with pivaloyl chloride and the lithium salt of the chiral alcohol.

The compound of formula V wherein A is a chiral auxiliary group and Q is hydrogen, —CH$_2$CH$_2$Ph-4-OSO$_2$CH$_3$ or R$^q$, wherein R$^q$ is as defined above, and the compound of formula VI, wherein Q is hydrogen, —CH$_2$CH$_2$Ph-4-OSO$_2$CH$_3$ or R$^q$ and R$^x$ is hydrogen or R$^p$, wherein R$^q$ and R$^p$ are as defined above, can be prepared by reduction of a compound of formula VII

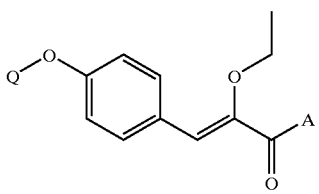

VII wherein A is a chiral auxiliary group, —OH, or —OR$^p$ wherein R$^p$ is as defined above and Q is hydrogen, —CH$_2$CH$_2$Ph-4-OSO$_2$CH$_3$ or R$^q$ wherein R$^q$ is as defined above, and if desired followed by removal of protecting groups.

The reduction of the olefin may be carried out by using a wide variety of reducing methods known to reduce carbon—carbon double bonds, such as catalytic hydrogenation in the presence of an appropriate catalyst or hydrogen transfer reagents such as diethyl-2,5-dimethyl-1,4-dihydropyridine-3,5-dicarboxylate.

The catalytic hydrogenation can be performed in alcohol, cellosolves, protic polar organic solvents, ethers, lower alifatic acids, and particularly in methanol, ethanol, methoxyethanol, dimethylformamide, tetrahydrofuran, dioxane, dimetoxyethane, ethyl acetate or acetic acid either used alone or in mixture. Examples of the catalysts used include palladium black, palladium on charcoal, platinum oxide or Wilkinson's catalyst. This reaction can be performed at different temperatures and pressures depending on the reactivity of the aimed reaction.

In case of hydrogen transfer reaction with diethyl-2,5-dimethyl-1,4-dihydropyridine-3,5-dicarboxylate the reaction can be conducted by mixing equimolar amounts of reactants and warming the mixture to melting (140–250° C.) in inert atmosphere or in vacuum.

The compound of formula VII wherein A is a chiral auxiliary group, —OH, or —OR$^p$, wherein R$^p$ is as defined above and Q is hydrogen, —CH$_2$CH$_2$Ph-4-OSO$_2$CH$_3^-$ or R$^q$, wherein R$^q$ is as defined above, can be prepared by a condensation reaction, such as a Knoevenagel or Wittig type reaction, of a carbonyl compound of the formula VIII

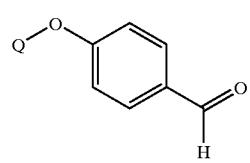

VIII wherein Q is hydrogen, —CH$_2$CH$_2$Ph-4-OSO$_2$CH$_3$ or R$^q$, wherein R$^q$ is as defined above, with a compound of the formula IX

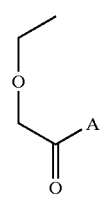

IX in which formula A is a chiral auxiliary group, —OH or —OR$^p$, wherein R$^p$ is as defined above, or a compound of the formula X

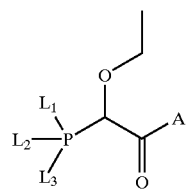

X in which formula A is a chiral auxiliary group or —OR$^p$, wherein R$^p$ is as defined above, L$^1$=L$^2$=L$^3$ are phenyl or $L^1=L^2$ are —Oalkyl and $L^3$ is =O, and, if desired, followed by removal of protecting groups or by an arylation reaction as described in for example Cacchi S., Ciattini P. G., Morera E., Ortar G., Tetrahedron Letters, 28 (28) 1987, pp 3039–3042.

In the condensation step, approximately equimolar amounts of reactants are mixed in the presence of a base, to provide the olefin compound. This step may be carried out in the presence of an inert solvent or in the absence of a solvent at a temperature between −20° C. and the melting point for the mixture. It might be necessary to add a dehydrating agent in order to achieve the olefinic compound.

In a typical such reaction the compounds of formula VIII and formula IX are mixed in a solvent such as tetrahydrofuran. Anhydrous potassium tert-butoxide is slowly added at low temperature i.e. −20° C. The reaction is quenched with acetic acid. The crude product is isolated, redissolved in toulene and refluxed with p-toluene sulfonic acid in a Dean-Stark apparatus. The solution is cooled and the product is isolated and purified according to standard methods (see Groger T., Waldmann E., Monatsh Chem 89, 1958, p 370).

The condensation step could also be performed as a Wittig-type reaction (see for example Comprehensive Organic Synthesis vol. 1 p. 755–781 Pergamon Press) or as described in the experimental part.

In a typical such reaction, approximately equimolar amounts of reactants of formula VIII and formula X are stirred in the presence of a base such as tetramethylguanidine or to potassium carbonate in a 1–5 fold molar excess. This step may be carried out in the presence of an inert solvent such as dichloromethane or acetonitrile and at a suitable temperature (−10° C.+60° C.) and at a time long enough.

The compound of the formula VIII when Q is —CH$_2$CH$_2$Ph-4-OSO$_2$CH$_3$ can be prepared by coupling a compound of the formula III wherein X is —OH or a leaving group such as a sulfonate or a halogen, with a compound of the formula XI

XI

When X is a leaving group such as a sulfonate or a halogen, the reaction may be performed as an alkylation reaction and when X is —OH, as a Mitsunobu reaction as described above.

D. The compound of formula I or formula II wherein A is —OR$^p$ and R$^p$ is as defined above and the compound of formula IV wherein A is OH or —OR$^p$ and Q is H or R$^q$ wherein R$^p$ and R$^q$ are as defined above can be prepared by enantiomeric separation, such as chiral chromatography of the compound of the formula V

V wherein A is —OH or —OR$^p$, Q is H, —CH$_2$CH$_2$Ph-4-OSO$_2$CH$_3$ or R$^q$ wherein R$^p$ and R$^q$ are as defined above.

E. The compound of the formula I or the formula II wherein A is a chiral auxiliary group or —OR$^p$, wherein R$^p$ is as defined above, and the compound of formula IV wherein A is a chiral auxiliary group, —OH, or —OR$^p$, wherein R$^p$ is as defined above and Q is hydrogen or R$^q$, wherein R$^q$ is as defined above and, can be prepared by asymmetric reduction of a compound of the formula VII

VII wherein A is a chiral auxiliary group, —OH, or —OR$^p$, wherein R$^p$ is as defined above and Q is hydrogen, —CH$_2$CH$_2$Ph-4-OSO$_2$CH$_3$ or R$^q$ wherein R$^q$ is as defined above.

The asymmetric reduction can be carried out using a wide variety of reducing methods known to reduce carbon—carbon double bonds such as catalytic hydrogenation in the presence of an appropriate chiral catalyst such as RH-BINAP or [Et-DuPHOS-Rh(COD)] or catalytic hydrogenation with an appropriate catalyst, such as palladium on charcoal using the chiral auxiliary group to induce the asymmetry.

The catalytic hydrogenation can be carried out in a wide variety of solvents, such as alcohol, cellosolves, protic polar organic solvents, ethers, lower alifatic acids, and particularly in methanol, ethanol, methoxyethanol, dimethylformamide, tetrahydrofuran, dioxane, dimetoxyethane, ethyl acetate or acetic acid, either used alone or in a mixture. The reaction can proceed at different temperatures and pressures depending on the reactivity of the aimed reaction.

F. The compound of the formula I or the formula II, wherein A is a chiral auxiliary group, or —OR$^p$, wherein R$^p$ is as defined above, and the compound of formula IV wherein A is a chiral auxiliary group, —OH, or —OR$^p$, wherein R$^p$ is as defined above and Q is hydrogen or R$^q$, wherein R$^q$ is as defined above, can be prepared by alkylating a compound of the formula XII

XII wherein A is a chiral auxiliary group, —OH, or —OR$^p$, wherein R$^p$ is as defined above, and Q is hydrogen, —$CH_2CH_2Ph$-4-$OSO_2CH_3$ or $R^q$, wherein $R^q$ is as defined above, with the required stereochemistry dependent on the reaction conditions used.

The alkylation may be carried out using a variety of alkylating agents, such as ethyl halide or diethyl sulfate (see for example Benedict D. R., Bianchi T. A., Cate L. A., Synthesis (1979), pp. 428–429, Barluenga J., Alonso-Cires L., Campos P. J., Asensio G., Synthesis, 1983, p. 53–55, Bull Chem Soc Jpn, 1986, 59, 2481, S. Patai, The Chemistry of the Ether Linkage, Wiley-Interscience NY, 1967, 445–498 or Survey of Organic Synthesis vol 1, Wiley-Interscience 1970, NY, p. 285–328).

The compound of formula XII wherein A is a chiral auxiliary group, —OH, or —$OR^p$, wherein $R^p$ is as defined above, and Q is hydrogen, —$CH_2CH_2Ph$-4-$OSO_2CH_3$ or $R^q$, wherein $R^q$ is as defined above, can be prepared by asymmetric reduction of a compound of the formula XIII

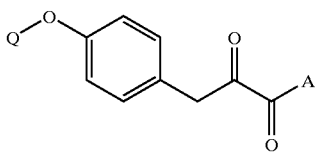

XIII wherein A is a chiral auxiliary group, —OH, or —$OR^p$, wherein $R^p$ is as defined above, and Q is hydrogen, —$CH_2CH_2Ph$-4-$OSO_2CH_3$ or $R^q$, wherein $R^q$ is as defined above.

The asymmetric reduction may be performed by using a wide variety of reducing methods which are known to reduce ketones enantioselectively (see Flynn G. A., Beight D. W., Tetrahedron Letters, 29(4), 1988, pp. 423–426).

The compound of formula XII wherein A is a chiral auxiliary group and Q is hydrogen, —$CH_2CH_2Ph$-4-$OSO_2CH_3$ or $R^q$, wherein $R^q$ is as defined above, may also be prepared by induced chiral reduction of a compound of formula XIII, wherein A is a chiral auxiliary group and Q is hydrogen, —$CH_2CH_2Ph$-4-$OSO_2CH$, or $R^q$, wherein $R^q$ is as defined above (see Xiang Y. B., Snow K., Belley M., J. Org. Chem., 1993, 58, pp 993–994).

The compound of formula XII, wherein A is a chiral auxiliary group, —OH or —$OR^p$, wherein $R^p$ is as defined above, and Q is hydrogen, —$CH_2CH_2Ph$-4-$OSO_2CH_3$ or $R^q$, wherein $R^q$ is as defined above, can be prepared by converting a compound of the formula XIV

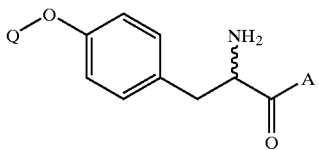

XIV wherein A is a chiral auxiliary group, —OH or —$OR^p$, wherein $R^p$ is as defined above, and Q is hydrogen, —$CH_2CH_2Ph$-4-$OSO_2CH_3$ or $R^q$, wherein $R^q$ is as defined above, with the required stereochemistry, dependent on the reaction conditions used (see for example K. Koga, C. C. Wu and S. Yamada, Tetrahedron Letters, no. 25, 1971, p 2283–2286, Kunz H., Lerchen H-G., Tetrahedron Letters, 28 (17) 1987, pp.1873–1876).

G. The compound of formula II, wherein A is a chiral auxiliary group, and the compound of formula IV wherein A is a chiral auxiliary group and Q is $R^q$, wherein $R^q$ is as defined above, can be prepared by reacting a compound of formula XV

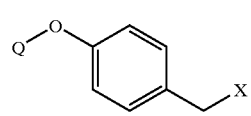

XV wherein X is a leaving group, such as a halogen or a sulfonate, and Q is —$CH_2CH_2Ph$-4-$OSO_2CH_3$ or $R^q$, wherein $R^q$ is as defined above, with a compound of the formula IX

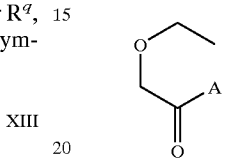

IX wherein A is a chiral auxiliary group.

In the alkylation step the compound of formula XV is reacted with a compound of formula IX in the presence of one or more bases such as potassium carbonate, triethylbenzyl-ammonium chloride, sodium hydride, LDA, butyllithium or LHMDS in an inert solvent such as acetonitrile, DMF or dichloromethane at a suitable temperature and time. The reaction can be carried out using standard methods known in the litterature. (see for example Pearsson W. H., Cheng M. C., J. Org. Chem., 51 (19) 1986, 3746–3748, Myers A. G., Yang B. H., Gleason J. L., J. Am. Chem. Soc. 1994,116, pp 9361–9362, Negrete G. R., Konopelski J. P., Tetrahedron Assymetry, 2,2, pp. 105–108, 1991, Davies S. G., Sanganee H. J., Tetrahedron Assymetry, 6,3, pp. 671–674, 1995, Hulin B., Newton L. S., Lewis D. M., Genereux P. E., Gibbs E. M., Clark D. A. J. Med.Chem. 39, 3897–3907 (1996) and Savignac M., Durand J-O, Genet J-P, Tetrahedron Assymetry, 5,4, pp.717–722, 1994).

The compound of formula XV wherein X is a leaving group, such as a halogen or a sulfonate, and Q is —$CH_2CH_2Ph$-4-$OSO_2CH_3$ or $R^q$, wherein $R^q$ is as defined above, can be prepared from a compound of formula XVI

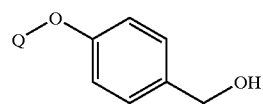

XVI wherein Q is —$CH_2CH_2Ph$-4-$OSO_2CH_2$ or $R^q$ wherein $R^q$ as defined above, using standard methods known to anyone skilled in the art.

The compound of formula XVI wherein Q is —$CH_2CH_2Ph$-4-$OSO_2CH_3$ or $R^q$, wherein $R^q$ is as defined above, can be prepared by reduction of a compound of formula VIII, wherein Q is —$CH_2CH_2Ph$-4-$OSO_2CH_3$ or $R^q$ wherein $R^q$ is as defined above, by standard methods known to anyone skilled in the art.

H. The compound of the invention of formula I and the compound of formula IV, wherein A is —OH and Q is hydrogen or $R^q$, wherein $R^q$ is as defined above, can be prepared by resolution of the racemate thereof and, if desired, followed by neutralization. The resolution can be performed by separative crystallization of a salt consisting of the racemate of, either the compound of the invention of formula I, or the compound of formula IV, and a chiral base, such as quinine, in an inert solvent such as ethyl acetate or toluene (see for example Duhamel P., Duhamel L., Danvy D., Plaquevent J. C., Giros B., Gros C., Schwartz J. C., Lecomte J. M., U.S. Pat. No. 5,136,076, Stephani R., Cesare V., J. Chem. Ed., 10, 1997, p. 1226 and Yamamoto M., Hayashi M., Masaki M., Nohira H., Tetrahedron Assymetry, 2,6, pp. 403–406, 1991).

The compounds of the invention may be isolated from their reaction mixtures using conventional techniques.

Persons skilled in the art will appreciate that, in order to obtain the compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceeding methods of preparation A-H, where necessary, hydroxy, amino or other reactive groups may be protected using a protecting group, $R^p$ or $R^q$ as described in the standard text "Protective groups in Organic Synthesis", $2^{nd}$ Edition (1991) by Greene and Wuts. The protecting group $R^p$ or $R^q$ may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Unless otherwise stated or indicated the term chiral auxiliary group denotes a chiral group, such as a chiral alcohol or amine, for instance (−)-menthol, (+)-isomenthol, (−)-norneol, (R)-2-phenyl glycinol, (S)-2-phenyl glycinol, (R)-4-phenyl-2-oxazolidinone or (S)-4-benzyl-2-oxazolidinone, which when connected to a carbonyl group easily can be cleaved to the corresponding acid.

Intermediates

When preparing the compound of formula I of the invention an intermediate of the formula IV

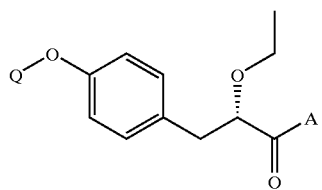

IV wherein Q is hydrogen and A is —OH or —OR$^p$, wherein R$^p$ is a protective group, e.g. ethyl, or A is a chiral auxiliary group, such as a chiral amine, e.g. (R)-fenylglycinol, or a chiral alcohol, such as menthol or a chiral oxazolidinone, such as (S)-4-benzyl-2-oxazolidineone, is particularly useful. It is prepared as described above. Under the same heading its use as intermediate for the preparation of the end compound of the invention is described.

Pharmaceutical Preparations

The compound of the invention will normally be administered via the oral, parenteral, intravenous, buccal, rectal, vaginal, transdemal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

The compound of the invention may also be combined with other therapeutic agents which are useful in the treatment of disorders associated with the development and progress of atherosclerosis such as hypertension, hyperlipidemias, dyslipidemias, diabetes and obesity.

Suitable daily doses of the compound of the invention in therapeutical treatment of humans are about 0.005–5 mg/kg body weight, preferably 0.01–0.5 mg/kg body weight.

According to a further aspect of the invention there is thus provided a pharmaceutical formulation including the compound of the invention, or pharmaceutically acceptable derivatives thereof, in optional admixture with pharmaceutically acceptable adjuvants, diluents and/or carriers.

Pharmacological Properties

The present compound of formula (I) will be adapted for prophylaxis and/or treatment of clinical conditions associated with reduced sensitivity to insulin (insulin resistance) and associated metabolic disorders. These clinical conditions will include, but will not be limited to, abdominal obesity, arterial hypertension, hyperinsulinaemia, hyperglycaemia (non insulin dependent diabetes mellitus (NIDDM)) and the dyslipidaemia (plasma lipoprotein disturbances) characteristically appearing with insulin resistance. This dyslipidaemia, also known as the atherogenic lipoprotein profile of phenotype B, is characterised by moderately elevated non-esterified fatty acids, elevated very low density lipoproteins (VLDL) triglycerides, low high density lipoproteins (HDL) cholesterol and the presence of small, dense, low density lipoproteins (LDL). Treatment with the present compound is expected to lower the cardiovascular morbidity and mortality associated with atherosclerosis. These cardiovascular disease conditions include macro-angiophaties causing myocardial infarction, cerebrovascular disease and peripheral arterial insufficiency of the lower extremities. Because of their insulin sensitizing effect the compound of formula (I) is also expected to reduce the progress of clinical conditions associated with chronic hyperglycaemia in diabetes like the micro-angiophaties causing renal disease and retinal damage. Furthermore the compound may be useful in treatment of various conditions outside the cardiovascular system associated with insulin resistance like the polycystic ovarian syndrome. The compound of the invention is a non-toxic insulin sensitizing agent with surprisingly good therapeutic effect and pharmacokinetic properties is and without undesirable weight gain.

General Experimental Procedures $^1$H NMR and $^{13}$C NMR measurements were performed on a BRUKER ACP 300 and Varian UNITY plus 400 and 500 spectrometers, operating at $^1$H frequencies of 300, 400 and 500 MHz respectively, and at $^{13}$C frequencies of 75, 100 and 125 MHz respectively.

Unless otherwise stated, chemical shifts are given in ppm with the solvent as internal standard.

WORKING EXAMPLES

Example 1

(S)-2-Ethoxy-3-[4-(2-{4-methanesulfonyl-oxyphenyl}ethoxy)phenyl]propanoic acid a) 2-(4-Methanesulfonyloxyphenyl)ethylmethanesulfonate p-Hydroxyphenethylalcohole (15 g; 0.108 mole) was dissolved in dichloromethane. Triethylamine (27.3 g; 0.27 mole) was added followed by addition of a solution of methanesulfonyl chloride (27.2 g; 0.239 mole) in dichloromethane at 0° C. The reaction mixture was allowed to reach room temperature, then stirred at room temperature and followed by TLC. The reaction mixture was filtered and the filtrate was washed with water. The organic phase was dried with sodium sulfate and then evaporated in vacuo to give 28 g (yield 88%) of 2-(4,methanesulfonyloxyphenyl) ethylmethanesulfonate.

$^1$H-NMR (400 MHz; CDCl$_3$): δ 2.85 (s, 3H), 3.05 (t, 2H), 3.15 (s, 3H), 4.35 (s, 2H), 7.2 (dm, 2H), 7.25 (dm, 2H).

$^{13}$C-NMR (100 MHz; CDCl$_3$): δ 34.8, 37, 27, 37, 31, 69.6, 122.2, 130.5, 135.8, 148.1.

b) 4-[2-(4-Formylphenoxy)ethyl]phenylmethanesulfonate 2-(4-Methanesulfonyloxyphenyl)ethylmethanesulfonate (30 g; 0.102 mole) was dissolved in acetonitrile and slowly added to a mixture of p-hydroxybenzaldehyde (31.1 g; 0.255 mole) and potassium carbonate (41.46 g; 0.3 mole) in acetonitrile. The resulting mixture was refluxed until 2-(4-methanesulfonyloxyphenyl)ethylmethanesulfonate was consumed. The salts were filtered off, the solvent was evaporated in vacuo, dichloromethane was added and the organic phase was washed with water. After evaporation of the solvent, purification by chromatography on silica gel using dichloromethane as eluant gave 21.6 g (yield 66%) of 4-[2-(4-formylphenoxy)ethyl]phenylmethanesulfonate.

$^1$H-NMR (400 MHz; CDCl$_3$): δ 3.05–3.15 (t, 2H+s, 3H), 4.2 (t, 2H), 6.95 (dm, 2H), 7.2 (dm, 2H), 7.3 (dm, 2H), 7.8 (dm, 2H), 9.8 (s, 1H).

$^{13}$C-NMR (100 MHz; CDCl$_3$): δ 37.3, 38.3, 63.4, 116.1, 122.1, 129.2, 130.6, 132.6, 138.1, 147.7, 162.6, 191.7.

c) 2-Ethoxy-3-{4-[2-(4-methanesulfonyloxyphenyl)ethoxy]phenyl}acrylic acid ethyl ester Tetramethylguanidine (9 g; 78 mmole) was slowly added to a solution of 4-[2-(4-formylphenoxy)ethyl] phenylmethanesulfonate (27 g; 84.2 mmole) and (1,2-diethoxy-2-oxyethyl)triphenylphosphonium chloride (30 g; 72 mmole) in chloroform (300 ml) at 0° C. After stirring at room temperature over night the solvent was evaporated in vacuo. Diethyl ether was added to the residue and insoluble material was filtered off. More diethyl ether was added and the mixture was filtered again. The filtrate was washed with sodium hydrogen carbonate solution. The organic phase was dried (magnesium sulfate) and the solvent was evaporated. Recrystallization of the residue in ethanol gave 20.2 g (yield 64.6%) of 2-ethoxy-3-{4-[2-(4-methanesulfonyloxyphenyl)-ethoxy]phenyl}acrylic acid ethyl ester.

$^1$H-NMR (500 MHz; CDCl$_3$): δ 1.34–1.38 (2t, 2×6H, J=7 Hz for both), 3.11 (t, 2H, J=6 Hz), 3.13 (s, 3H), 3.98 (q, 2H, J=7 Hz), 4.2 (t, 2H, 3=6.8 Hz), 4.28 (q, 2H, J=7 Hz), 6.87 (dm, 2H, J=9 Hz, unresolved), 6.95 (s, 1H), 7.23 (dm, 2H, J=9 Hz, unresolved), 7.33 (dm, 2H, J=9 Hz, unresolved), 7.73 (dm, 2H, J=9 Hz, unresolved).

$^{13}$C-NMR (125 MHz; CDCl$_3$): δ 14.3, 15.5, 35.0, 37.3, 61.0, 67.5, 68.1, 114.4, 122.0, 123.8, 126.6, 130.5, 131.7, 137.7, 143.1, 147.9, 159.0, 164.9.

d) 2-Ethoxy-3-[4-(2-{4-methanesulfonyloxyphenyl)ethoxy)phenyl]propanoic acid ethyl ester 2-Ethoxy-3-{4-[2-(4-methanesulfonyloxyphenyl)ethoxy]phenyl}acrylic acid ethyl ester (1.47 g; 3.38 mmole) was hydrogenated for 3 hours at atmospheric pressure in ethyl acetate (50 ml) using Pd/C (5%; 0.75 g) as catalyst. The reaction mixture was filtered through celite and dried (magnesium sulfate). The solvent was evaporated in vacuo to give 1.44 g; yield 98%) of 2-ethoxy-3-[4-(2-{4-methanesulfonyloxyphenyl}-ethoxy)phenyl]propanoic acid ethyl ester.

$^1$H-NMR (500 MHz; CDCl$_3$): δ 1.16 (t, 3H, J=7 Hz), 1.23 (t, 3H, J=7 Hz), 2.92–2.96 (m, 2H), 3.09 (t, 2H, J=6.6), 3.13 (s, 3H), 3.31–3.38 (m, 1H), 3.56–3.63 (m, 1H), 3.94–3.98 (m, 1H), 4.12–4.19 (m, 4H), 6.8 (dm, 2H, J=8.8 Hz, unresolved), 7.14 (dm, 2H, J=8.9 Hz, unresolved), 7.22 (dm, 2H, J=8.9 Hz, unresolved), 7.33 (dm, 2H, J=8.6 Hz, unresolved). $^{13}$C-NMR (125 MHz; CDCl$_3$): δ 14.2, 15.0, 35.1, 37.2, 38.4, 60.7, 66.1, 68.1, 80.3, 114.3, 121.9, 129.5, 130.4, 130.5, 138.0, 147.8, 157.4, 172.5.

e) 2-Ethoxy-3-[4-(2-{4-methanesulfonyloxyphenyl}ethoxy) phenyl]propanoic acid

Lithium hydroxide hydrate (0.12 g; 2.82 mmole) dissolved in water (10 ml) was slowly added to a solution of 2-ethoxy-3-[4-(2-{4-methanesulfonyloxy-phenyl}ethoxy) phenyl]propanoic acid ethyl ester (1.12 g; 2.56 mmole) in tetrahydrofuran (30 ml). After stirring at room temperature for 3 hours, water (50 ml) was added and tetrahydrofuran was removed by evaporation in vacuo. The water residue was acidified with hydrochloric acid (2M) and extracted three times with ethyl acetate. The organic phase was dried (magnesium sulfate), filtered and the solvent was evaporated in vacuo to give 1 g (yield 96%) of 2-ethoxy-3-[4-(2-{4-methanesulfonyloxyphenyl}ethoxy)-phenyl]propanoic acid.

$^1$H-NMR (500 MHz; CDCl$_3$): δ 1.17 (t, 3H, J=7 Hz), 2.91–2.99 (m, 1H), 3.03–3.11 (m, 3H), 3.12 (s, 3H), 3.39–3.47 (m, 1H), 3.57–3.64 (m, 1H), 4.01–4.06 (m, 1H), 4.14 (t, 2H, J=6.7 Hz), 6.81 (dm, 2H, J=8.6 Hz, unresolved), 7.15 (dm, 2H, J=8.6 Hz, unresolved), 7.22 (dm, 2H, J=8.6 Hz, unresolved), 7.33 (dm, 2H, J=8.6 Hz, unresolved).

$^{13}$C-NMR (125 MHz; CDCl$_3$): δ 15.0, 35.1, 37.2, 37.8, 66.8, 68.1, 79.7, 114.4, 121.9, 128.8, 130.49, 130.52, 137.9, 147.8, 157.5, 169.1.

f) (S)-2-ethoxy-N-(2-hydroxy-(R)-1-phenylethyl)-3-[4-(2-{4-methanesulfonyloxyphenyl}-ethoxy)phenyl]propanoic amide.

A solution of 2-ethoxy-3-[4-(2-{4-methanesulfonyloxyphenyl} ethoxy)phenyl]propanoic acid (10.5 g; 25.7 mmole) in dry dichloromethane (150 ml) was cooled on an ice-bath and EDC (5.42 g; 28.3 mmole), diisopropylethylamine (4.8 ml; 28.3 mmole) and HOBtxH$_2$O (3.82 g; 28.3 mmole) were added. After 20 minutes the ice-bath was removed and (R)-phenylglycinol (3.88 g; 28.3 mmole) was added. After stirring at room temperature over night dichloromethane (100 ml), citric acid (60 ml, 10%) and ethyl acetate were added and the phases were separated. The organic phase was washed with citric acid (60 ml), sodium bicarbonate (2×60 ml) and brine (60 ml), dried (sodium sulfate), filtered and the solvent evaporated in vacuo. The crude product was crystallized twice in ethyl acetate/heptan to give 4.43 g of (R)-2-ethoxy-N-(2-hydroxy-(R)-1-phenylethyl)-3-[4-(2-{4-methanesulfonyloxyphenyl}ethoxy)phenyl]propanoic amide. The mother liquids were combined, the solvent was evaporated in vacuo and the residue was purified by chromatography on silica gel using ethyl acetate:heptan (gradient 25 to 100% ethyl acetate) to give 5.14 g (yield 38%) of (S)-2-ethoxy-N-(2-hydroxy-(R)-1-phenylethyl)-3-[4-(2-{4-methanesulfonyloxyphenyl}ethoxy)-phenyl]propanoic amide and 0.51 g (totally 4.94 g, yield 36%) of (R)-2-ethoxy-N-(2-hydroxy-(R)-1-phenylethyl)-3-[4-(2-{4-methanesulfonyloxyphenyl}-ethoxy)phenyl]propanoic amide.

$^1$H-NMR (600 MHz; DMSO-d$_6$): δ 1.04 (t, 3H, J=7.0 Hz), 2.74 (dd, 1H, J=13.9 and 7.6 Hz), 2.84 (dd, 1H, J=13.9 and 5.3 Hz), 3.05 (t, 2H, J=6.7 Hz), 3.30 (m, 1H), 3.34 (s, 3H), 3.44 (m, 1H), 3.55 (t, 2H, J=5.8 Hz), 3.88 (dd, 1H, J=7.3 and 5.5 Hz), 4.15 (t, 2H, J=6.7 Hz), 4.83 (m, 1H), 4.85 (t, 1 OH, J=5.4 Hz), 6.80 (d, 2H, J=8.4 Hz), 7.09 (d, 2H, J=8.4 Hz), 7.17 (m, 3H), 7.23 (m, 2H), 7.28 (d, 2H, J=8.3 Hz), 7.43 (d, 2H, J=8.3 Hz), 8.06 (d, 1 NH, J=8.2 Hz).
$^{13}$C-NMR (150 MHz; DMSO-$d_6$): δ 15.2, 34.4, 37.5, 38.0, 54.6, 64.5, 65.1, 67.9, 81.1, 114.2, 122.2, 126.8, 127.0, 128.1, 129.8, 130.4, 130.7, 138.1, 141.2, 147.8, 157.0, 171.1.

g) (S)-2-Ethoxy-3-[4-(2-{4-methanesulfonyl-oxyphenyl}ethoxy)phenyl]propanoic acid (S)-2-Ethoxy-N-(2-hydroxy-(R)-1-phenylethyl)-3-[4-(2-{4-methanesulfonyloxyphenyl}ethoxy)phenyl]propanoic amide (4.49 g; 8.59 mmole), concentrated sulfuric acid (12.5 ml), dioxan (50 ml) and water (50 ml) were stirred at 80° C. for 6 hours. After cooling, water (100 ml) was added and the product was extracted with dichloromethane (2×100 ml). The organic phases were combined and washed with brine (60 ml), dried (sodium sulfate), filtered and evaporated in vacuo. Purification by chromatography on silica gel using heptan:ethyl acetate:acetic acid (10:10:1) as gradient and azeotropic destination with toluen gave 2.78 g (yield 79%) of (S)-2-ethoxy-3-[4-(2-{4-methanesulfonyloxyphenyl}ethoxy)phenyl]propanoic acid.

$^{1}$H-NMR (600 MHz; DMSO-$d_6$): δ 1.02 (t, 3H, J=7.0 Hz), 2.78 (dd, 1H, J=13.9 and 8.0 Hz), 2.86 (dd, 1H, J=13.9 and 5.2 Hz), 3.04 (t, 2H, J=6.8 Hz), 3.28 (dq, 1H, J=9.1 and 7.0 Hz), 3.35 (s, 3H), 3.49 (dq, 1H, J=9.1 and 7.0 Hz), 3.92 (dd, 1H, J=5.2 and 7.7 Hz), 4.15 (t, 2H, J=6.8 Hz), 6.82 (d, 2H, J=8.7 Hz), 7.11 (d, 2H, J=8.7 Hz), 7.27 (d, 2H, J=8.5 Hz), 7.42 (d, 2H, J=8.5 Hz), 12.59 (s, br, 1 OH).
$^{13}$C-NMR (150 MHz; DMSO-$d_6$): 8 15.2, 34.4, 37.5, 37.7, 65.0, 67.9, 79.4, 114.2, 122.2, 129.6, 130.4, 130.7, 138.0, 147.8, 157.1, 173.4.

Example 2

(S)-2-Ethoxy-3-[4-(2-{4-methanesulfonyloxyphenyl}ethoxy)phenyl]propanoic acid a) 3-(4-Benzyloxyphenyl)-2-ethoxyacrylic acid ethyl ester Tetramethylguanidine (33 g; 0.286 mole) was added to a solution of 4-benzyloxybenzaldehyde (59.1 g; 0.278 mole) and (1,2-diethoxy-2-oxyethyl) (triphenyl) phosphoniun chloride (101.8 g; 0.237 mole) in dichloromethane (600 ml) at 0° C. After stirring at room temperature over night, the solvent was evaporated in vacuo. The residue was dissolved in diethyl ether, insoluble material was filtered off and the filtrate was vaporated. The residue was stirred over night with sodium bisulfite (saturated water solution) and diethyl ether. The solid material was filtered off, the filtrate was extracted with diethyl ether, dried (magnesium sulfate) and the solvent was evaporated in vacuo. Purification of the crude product by flash chromatography and crystallization in isopropanol gave 66.8 g (yield 86.3%) of 3-(4-benzyloxyphenyl)-2-ethoxyacrylic acid ethyl ester.

$^{13}$C-NMR (125 MHz; CDCl$_3$): δ 14.4, 15.6, 61.0, 67.5, 70.0, 114.8, 124.0, 126.7, 127.5, 128.1, 128.6, 131.7, 136.7, 143.1, 159.2, 165.0.

b) 3-(4-Benzyloxyphenyl)-2-ethoxypropanoic acid ethyl ester 3-(4-Benzyloxyphenyl)-2-ethoxyacrylic acid ethyl ester (0.5 g; 1.5 nmole) was hydrogenated at atmospheric pressure using rhodium on charcoal as catalyst (5%, 50 mg) in methanol (20 ml). The crude product was purified by chromatography using heptane:ethyl acetate (5:1) as eluant to give 50 mg (yield 10%) of 3-(4-benzyloxyphenyl)-2-ethoxypropanoic acid ethyl ester.

$^{1}$H NMR (300 MHz; CDCl$_3$): δ 7.47–7.30 (m, 5H), 7.17 (d, J=8.8, 2H), 6.91 (d, J=8.8 Hz, 2H), 5.06 (s, 2H), 4.17 (q, J=7.2 Hz, 2H), 3.98 (t, J=6.6 Hz, 1H), 3.61 (dq, J=8.9 and 6.8 Hz, 1H), 3.36 (dq, J=8.9 and 6.8 Hz, 1H), 2.97 (d, J=6.6 Hz, 2H), 1.22 (t, J=7.2 Hz, 3H), 1.18 (t, J=6.8 Hz, 3H).
$^{13}$C NMR (75 MHz; CDCl$_3$): δ 172.6, 157.6, 137.1, 130.4, 129.5, 128.6, 127.9, 127.5, 114.6, 80.4, 70.0, 66.2, 60.8, 38.5, 15.1, 14.2.

c) 3-(4-Benzyloxyphenyl)-2-ethoxypropanoic acid

Lithium hydroxide hydrate (7.4 g; 177 mmole) dissolved in water (150 ml) was added to a solution of 3-(4-benzyloxyphenyl)-2-ethoxypropanoic acid ethyl ester (23.25 g; 70.8 mmole) in dioxan (150 ml). After stirring at room temperature over night dioxan was evaporated in vacuo, water was added and the mixture was washed with diethyl ether. The water phase was acidified with hydrochloric acid (1 M) and extracted with ethyl acetate. The organic phase was washed with water and brine, dried and the solvent was evaporated in vacuo to give 21.1 g (yield 99.2%) of 3-(4-benzyloxyphenyl)-2-ethoxypropanoic acid.

$^{1}$H NMR (300 MHz; CDCl$_3$): δ 1.15 (t, 3H), 2.9–3.1 (m, 2H), 3.35–3.45 (m, 1H), 3.6–3.7 (m, 1H), 3.95–3.41 (m, 1H), 5.05 (s, 2H), 6.95 (d, 2H), 7.2 (d, 2H), 7.25–7.5 (m, 5H). $^{13}$C NMR (75 MHz; CDCl$_3$): δ 15.0, 38.1, 66.6, 70.0, 79.9, 114.7, 127.5, 128.0, 128.6, 129.3, 130.5, 137.1, 157.7, 176.3.

d) 3-(4-Benzyloxyphenyl)-(S)-2-ethoxy-N-(2-hydroxy-(R)-1-phenylethyl)propanoic amide A solution of 3-(4-benzyloxyphenyl)-2-ethoxypropanoic acid (2.92 g, 9.74 mmole) in dry dichloromethane (30 ml) was cooled on an ice-bath and EDC (2.03 g; 10.61 mmole), diisopropylethylamine (1.84 ml, 10.61 mmole) and HOBt x H$_2$O (1.43 g; 10.61 mmole) were added. After 30 minutes the ice-bath was removed and (R)-phenylglycinol (1.46 g, 10.61 mmole) was added. After stirring at room temperature over night ethyl acetate (100 ml) was added and the mixture was washed with potassium hydrogensulfate (1 M), saturated sodium bicarbonate solution, sodium carbonate solution and brine. The organic phase was dried (sodium sulfate), filtered and the solvent was evaporated in vacuo. The crude product was purified by chromatography on silica gel using ethyl acetate:heptan to give 1.5 g (yield 37%) of 3-(4-benzyloxyphenyl)-(S)-2-ethoxy-N-(2-hydroxy-(R)-1-phenylethyl)propanoic amide and 1.25 g (yield 31%) of 3-(4-benzyloxyphenyl)-(R)-2-ethoxy-N-(2-hydroxy-(R)-1-phenylethyl)propanoic amide.

$^{1}$H NMR (400 MHz; CDCl$_3$): δ 7.43–7.27 (m, 8H), 7.22 (d, J=8.3 Hz, 4H), 7.13 (d, NH, J=7.8 Hz, 1H), 6.96 (d, J=8.3 Hz, 1H), 5.08 (s, 2H), 5.01 (m, 1H), 3.99 (dd, J=6.8 and 3.9 Hz, 1H), 3.69 (m, 2H), 3.50 (q, J=6.8 Hz, 2H), 3.15 (dd, J=14.2 and 3.9 Hz, 1H), 2.97 (dd, J=14.2 and 6.8 Hz, 1H), 2.94 (m, OH, 1H), 1.16 (t, J=6.8 Hz, 3H).
$^{13}$C NMR (100 MHz; CDCl$_3$): δ 172.3, 157.5, 138.9, 137.0, 130.7, 129.4, 128.6, 128.4, 127.7, 127.6, 127.3, 126.5, 114.4, 81.0, 69.8, 66.3, 66.0, 55.3, 37.8, 15.1.

e) 3-(4-Benzyloxyphenyl)-(S)-2-ethoxypropanoic acid 3-(4-Benzyloxyphenyl)-(S)-2-ethoxy-N-(2-hydroxy-(R)-1-phenylethyl)propanoic amide (8.9 g; 21.22 mmole) was hydrolyzed with concentrated sulfuric acid (27 ml) in water (104 ml) and dioxane (104 ml) at 90° C. for 5 hours. The reaction mixture was poured onto water (220 ml) and extracted with ethyl acetate. The organic phase was washed with brine, dried (sodium sulfate) and the solvent was evaporated in vacuo to give 6.85 g of a mixture of 3-(4-benzyloxyphenyl)-2-(S)-ethoxypropanoic acid and (S)-2-ethoxy-3-(4-hydroxyphenyl)-propanoic acid, which was used without further purification.

$^{1}$H NMR (400 MHz; CDCl$_3$): δ 7.47–7.30 (m, 5H), 7.19 (d, J=8.8 Hz, 2H), 6.93 (d, J=8.8 Hz, 2H), 5.10 (s, 2H), 4.06 (dd, J=7.8 and 4.4 Hz, 1H), 3.64 (dq, J=9.8 and 6.8 Hz, 1H), 3.44

(dq, J=9.8 and 6.8 Hz, 1H), 3.09 (dd, J=14.2 and 4.4 Hz, 1H), 2.98 (dd, J=14.2 and 7.8 Hz, 1H), 1.19 (t, J=6.8 Hz, 3H).

f) 3-(4-Benzyloxyphenyl)-(S)-2-ethoxypropanoic acid ethyl ester

Hydrogen chloride (g) was bubbled through a solution of 3-(4-benzyloxyphenyl)-2-(S)-ethoxypropanoic acid (6.85 g) in ethanol (400 ml). Thionyl chloride (2 ml, 27.4 mmole) was slowly added and the reaction mixture was refluxed for 2 hours. The solvent was evaporated in vacuo to give 8 g of a mixture of 3-(4-benzyloxyphenyl)-(S)-2-ethoxypropanoic acid ethyl ester and (S)-2-ethoxy-3-(4hydroxyphenyl) propanoic acid ethyl ester which was used without further purification.

$^1$H NMR (300 MHz; $CDCl_3$): δ 7.47–7.30 (m, 5H), 7.17 (d, J=8.8, 2H), 6.91 (d, J=8.8 Hz, 2H), 5.06 (s, 2H), 4.17 (q, J=7.2 Hz, 2H), 3.98 (t, J=6.6 Hz, 1H), 3.61 (dq, J=8.9 and 6.8 Hz, 1H), 3.36 (dq, J=8.9 and 6.8 Hz, 1H), 2.97 (d, J=6.6 Hz, 2H), 1.22 (t, J=7.2 Hz, 3H), 1.18 (t, J=6.8 Hz, 3H).

$^{13}$C NMR (75 MHz; $CDCl_3$): δ 172.6, 157.6, 137.1, 130.4, 129.5, 128.6, 127.9, 127.5, 114.6, 80.4, 70.0, 66.2, 60.8, 38.5, 15.1, 14.2.

g) (S)-2-Ethoxy-3-(4-hydroxyphenyl)propanoic acid ethyl ester 3-(4-Benzyloxyphenyl)-(S)-2-ethoxypropanoic acid ethyl ester was hydrogenated at atmospheric pressure for 2 hours in ethyl acetate using Pd/C as catalyst. Purification by chromatography on silica gel using toluen:ethyl acetate as eluant gave 3.83 g (yield in 3 steps 76%) of (S)-2-ethoxy-3-(4-hydroxyphenyl)propanoic acid ethyl ester.

$^1$H-NMR (400 MHz; $CDCl_3$): δ 1.18 (t, 3H, J=6.8 Hz), 1.24 (t, 3H, J=7 Hz), 2.96 (d, 2H, J=6.5 Hz), 3.34–3.43 (m, 1H), 3.57–3.66 (m, 1H), 4.00 (t, 1H, 6.5 Hz), 4.18 (q, 2H, J=7 Hz), 5.30 (s, 1 OH), 6.74 (dm, 2H, J=8.5 Hz, unresolved), 7.10 (dm, 2H, J=8.5 Hz, unresolved).

$^{13}$C-NMR (100 MHz; $CDCl_3$): δ 14.2, 15.0, 38.4, 60.9, 66.2, 80.4, 115.1, 129.0, 130.5, 154.5, 172.7.

h) (S)-2-Ethoxy-3-[4-(2-{4-methanesulfonyloxyphenyl} ethoxy)phenyl]propanoic acid ethyl ester A solution of 2-(4-methanesulfonyloxyphenyl) ethylmethanesulfonate (described in Example 1a) (2.41 g; 8.14 mmole) in acetonitrile (11.8 ml) was added to a mixture of (S)-2-ethoxy-3-(4-hydroxyphenyl)propanoic acid ethyl ester (1.3 g; 5.46 mmole), potassium carbonate (2.26 g; 16.4 mmole) and magnesium sulfate (1 g) in acetonitrile (50 ml). The reaction mixture was refluxed for 19 hours. More of 2-(4-methanesulfonyloxyphenyl)ethyl-methanesulfonate (0.8 g; 2.73 mmole) was added and the reaction mixture was refluxed for another 25 hours. Solid material was filtered off and the solvent was evaporated in vacuo to give 3.6 g of (S)-2-ethoxy-3-[4-(2-{4-methanesulfonyloxyphenyl}ethoxy)phenyl]-propanoic acid ethyl ester.

i) (S)-2-Ethoxy-3-[4-(2-{4-methanesulfonyl-oxyphenyl}ethoxy)phenyl]propanoic acid Lithium hydroxide hydrate (0.229 g; 5.45 mmole) dissolved in water (6 ml) was slowly added to a mixture of (S)-2-ethoxy-3-[4-(2-{4-methanesulfonyloxyphenyl} ethoxy)phenyl]-propanoic acid ethyl ester (2.29 g; 5.24 mmole) in tetrahydrofuran (50 ml) and water (10 ml) at 5° C. The reaction mixture was stirred at 5° C. for 2.5 hours, at 20° C. for 3 hours, at 0° C. for 15 hours and at 20° C. for 3,5 hours. More lithium hydroxide hydrate (44 mg, 1.05 mmole) dissolved in water (1 ml) was added at 10° C. After another 21.5 hours of stirring at 10° C., more lithium hydroxide hydrate (44 mg; 1.05 mmole) dissolved in water (1 ml) was added. The reaction mixture was stirred at 25° C. for 3 hours and then kept at 2° C. for 67 hours. Tetrahydrofuran was evaporated in vacuo and then water and ethyl acetate were added. Insoluble material was filtered off and the phases of the filtrate were separated. The water phase was washed twice with ethyl acetate, acidified with hydrochloric acid (2 M; 3.2 ml) and extracted with ethyl acetate (30 ml). The organic phase was washed twice with water, dried (magnesium sulfate), filtered and the solvent was evaporated in vacuo to give 1.9 g (yield 72% in 2 steps) of (S)-2-ethoxy-3-[4-(2-{4-methanesulfonyloxyphenyl}-ethoxy)phenyl]propanoic acid.

$^1$H-NMR (600 MHz; DMSO-$d_6$): δ 1.02 (t, 3H, J=7.0 Hz), 2.78 (dd, 1H, J=13.9 and 8.0 Hz), 2.86 (dd, 1H, J=13.9 and 5.2 Hz), 3.04 (t, 2H, J=6.8 Hz), 3.28 (dq, 1H, J=9.1 and 7.0 Hz), 3.35 (s, 3H), 3.49 (dq, 1H, J=9.1 and 7.0 Hz), 3.92 (dd, 1H, J=5.2 and 7.7 Hz), 4.15 (t, 2H, J=6.8 Hz), 6.82 (d, 2H, J=8.7 Hz), 7.11 (d, 2H, J=8.7 Hz), 7.27 (d, 2H, J=8.5 Hz), 7.42 (d, 2H, J=8.5 Hz), 12.59 (s, br, 1 OH).

$^{13}$C-NMR (150 MHz; DMSO-$d_6$): δ15.2, 34.4, 37.5, 37.7, 65.0, 67.9, 79.4, 114.2, 122.2, 129.6, 130.4, 130.7, 138.0, 147.8, 157.1, 173.4.

Biological Activity

The biological activity of the compound of the invention was tested in obese diabetic mice of the Umeå ob/ob strain. Groups of mice received the test compound by gavage once daily for 7 days. On the last day of the experiment the animals were anesthetized 2h after dose in a non-fed state and blood was collected from an incised artery. Plasma was analyzed for concentration of glucose, insulin and triglycerides. A group of untreated obese diabetic mice of the same age served as control. The weight of the mice was measured before and after the experiment and the obtained weight gain was compared to the weight gain of the control animals. The individual values for glucose, insulin and triglyceride levels of the mice from the test group were expressed as the percent rage of the corresponding values from the control group.

The desired "therapeutic effect" was calculated as the average percent reduction of the three variables glucose, insulin and triglycerides below the levels in the control animals. The therapeutic effect of the tested compounds according to the invention was compared to the same effect in the prior art compound troglitazone, administrered by gavage in the oral dose of 100 μmol/kg for 7 days.

The superior effects of the tested compound according to the invention compared to that of troglitazone when given in the same oral dose demonstrate the increased potency and efficiacy of the claimed compound.

| | Abbreviations |
|---|---|
| NIDDM | non insulin dependent diabetes mellitus |
| VLDL | very low density lipoproteins |
| HDL | high density lipoproteins |
| IRS | insulin resistance syndrom |
| PPAR | peroxisome proliferator activated receptor |
| DEAD | diethyl azodicarboxylate |
| ADDP | azodicarbonyl dipiperidine |
| EDC | 1-(3-dimethylaminopropyl)-3-ethylcarbodiimide |
| EDCxHCl | 1-(3-dimethylaminopropyl)-3-ethylcarbodiimide hydrochloride |
| DCC | dicyclohexylcarbodiimide |
| HBTU | O-benzotriazol-1-yl-N,N,N',N'-tetramethyluronium hexafluorophosphate |

-continued

| Abbreviations | |
|---|---|
| TBTU | O-benzotriazol-1-yl-N,N,N',N'-tetramethyluronium tetrafluoroborate |
| PyBop | benzotriazole-1-yl-oxy-tris-pyrolidino-phosphonium hexafluorophosphate |
| DMF | dimethylformamide |
| DMAP | 4-dimethylaminopyridine |
| TEA | triethylamine |
| DiPEA | diisopropylethylamine |
| BINAP | 2,2'-bis(diphenylphosphino)-1,1'-binaphtyl |
| COD | cyclooctadiene |
| LDA | lithium diisopropylamide |
| LHMDS | lithium hexamethyldisilylamine |
| TLC | thin layer chromatography |
| THF | tetrahydrofuran |
| Pd/C | palladium on charcoal |
| HOBt x H2O | 1-hydroxybenzotriazole-hydrate |
| m | multiplet |
| t | triplet |
| s | singlet |
| d | doublet |
| q | quartet |
| qvint | quintet |
| br | broad |
| dm | multiplet of doublet |
| rac | racemate |

What is claimed is:

1. A compound of the formula IV

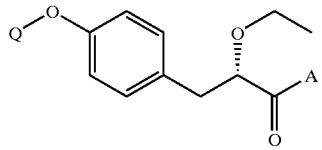

IV wherein Q is hydrogen and A is —OH, alkoxy having 1 to 3 carbon atoms, or a chiral auxiliary group selected from the group consisting of a chiral amine, a chiral alcohol, and a chiral oxazolidinone.

2. A compound according to claim 1, wherein in formula IV A is —OH or alkoxy having 1 to 3 carbon atoms.

3. A compound according to claim 1, wherein the chiral auxiliary group is selected from the group consisting of (−)-menthol, (+)-isomenthol, (−)-norneol, (R)-2-phenyl glycinol, (S)-2-phenyl glycinol, (R)-4-phenyl-2-oxazolidinone or (S)-4-benzyl-2-oxazolidinone.

4. A compound according to claim 1, wherein A is ethoxy.

5. A compound according claim 1, wherein A is hydroxy.

6. The compound (S)-2-ethoxy-3-(4-hydroxyphenyl) propanoic acid ethyl ester.

* * * * *

UNITED STATES PATENT AND TRADEMARK OFFICE
CERTIFICATE OF CORRECTION

PATENT NO. : 6,660,879 B2
DATED : December 9, 2003
INVENTOR(S) : Andersson

It is certified that error appears in the above-identified patent and that said Letters Patent is hereby corrected as shown below:

Title page,
Item [63], Related U.S. Application Data, should read -- Continuation of application serial no. 09/861,163, filed May 18, 2001 now abandoned, which is a continuation application of application serial no. 09/341,904, filed on Jul. 20, 1999, now U.S. Pat. No. 6,258,850, which is a 371 of PCT/SE99/00941, filed May 31, 1999. --

Column 1,
Lines 4-8, should read -- This application is a continuation of U.S. application Ser. No. 09/861,163, filed May 18, 2001, now abandoned, which is a continuation application of U.S. application Ser. No. 09/341,904, filed Jul. 20, 1999, now U.S. Pat. No. 6,258,850 B1, which is a 371 of PCT/SE99/00941, filed May 31, 1999. --

Signed and Sealed this

Twenty-third Day of March, 2004

JON W. DUDAS
*Acting Director of the United States Patent and Trademark Office*